United States Patent [19]
Martini et al.

[11] Patent Number: 6,120,704
[45] Date of Patent: Sep. 19, 2000

[54] MIXTURES OF OPTICAL BRIGHTENERS

[75] Inventors: Thomas Martini, Kelkheim; Helmut Neunzerling, Dornburg, both of Germany

[73] Assignee: Clariant GmbH, Frankfurt, Germany

[21] Appl. No.: 09/121,803

[22] Filed: Jul. 23, 1998

[30] Foreign Application Priority Data

Jul. 25, 1997 [DE] Germany ............... 197 32 109

[51] Int. Cl.⁷ ............... D06L 3/12; C09K 11/06
[52] U.S. Cl. ............... 252/301.21; 252/8.91; 252/301.22; 252/301.23; 252/301.24; 252/301.25; 252/301.27; 252/301.28; 252/301.29; 252/301.31; 252/301.32; 8/648; 8/922; 8/924
[58] Field of Search ............... 252/8.91, 301.21, 252/301.22, 301.23, 301.24, 301.25, 301.27, 301.28, 301.29, 301.31, 301.32; 8/648, 922, 924

[56] References Cited

U.S. PATENT DOCUMENTS

| | | | |
|---|---|---|---|
| 3,985,687 | 10/1976 | Inamorato et al. | 510/325 |
| 4,092,253 | 5/1978 | Cuntze et al. | 510/333 |
| 4,400,294 | 8/1983 | Martini et al. | 252/301.24 |
| 4,416,795 | 11/1983 | Martini et al. | 252/301.23 |
| 4,759,876 | 7/1988 | Crossin | 510/300 |
| 5,051,111 | 9/1991 | Anceschi et al. | 252/301.23 |

FOREIGN PATENT DOCUMENTS

| | | |
|---|---|---|
| 0033018 | 8/1981 | European Pat. Off. . |
| 0035694 | 9/1981 | European Pat. Off. . |
| 0058880 | 9/1982 | European Pat. Off. . |
| 0323399 | 7/1989 | European Pat. Off. . |
| 1955310 | 5/1971 | Germany . |
| 2839936 | 4/1980 | Germany . |
| 2032480 | 5/1980 | United Kingdom . |

OTHER PUBLICATIONS

Mettland Textilberberichte (65) May 1984, pp. 327–329.
Winnacker/Kuchler, Chem. Technologie (6), pp. 690–698 (No Date).
European Search Report (Dec. 1998).
Derwent Patent Family Report and/or Abstracts (Dec. 1998).
XP002085418 & JP 58025361 A (Nippon Kayaku KK) Feb. 15, 1983.
XP002085419 & JP 50025877 A (Nippon Kayaku KK) Mar. 18, 1975.

*Primary Examiner*—Anthony J. Green
*Attorney, Agent, or Firm*—Scott E. Hanf

[57] ABSTRACT

The invention relates to mixtures of optical brighteners comprising nonionic polyester brighteners and anionic or nonionic polyamide brighteners, which develop a synergistic effect. The brighteners of the invention are suitable for polyamide and polyurethane fabrics but also for blends of these fabrics with other natural or synthetic fibers.

7 Claims, No Drawings

MIXTURES OF OPTICAL BRIGHTENERS

BACKGROUND OF THE INVENTION

Synergistic effects when using mixtures of optical brighteners to brighten polyester (PES) textile materials are known and are widely used in the textile industry in order to achieve effect enhancements and cost savings. The effect of the synergy is observed following textile application, i.e. by applying the brightener mixture by the exhaust process or pad thermosol process. A review of the literature on interpretation of synergism is given in Melliand Textilberichte (65) 1984, 327–329.

The synergistic mixtures employed to date only develop their effect when the individual components of the optical brighteners for PES possess nonionic structures.

SUMMARY OF THE INVENTION

It has surprisingly now been found that in the brightening of polyamide (PA) and blends thereof with other fibers synergistic effects arise if a polyester brightener of nonionic structure is mixed with a PA brightener of anionic or nonionic structure, particularly good effect enhancements being achieved if one component of the mixture has a more reddish hue and the other a bluer hue. In this context, synergies have been obtained in respect not only of the white effects but also of the fastness properties, especially the light fastness and weather fastness properties.

DESCRIPTION OF THE INVENTION

The invention provides mixtures of optical brighteners comprising

A) at least one nonionic PES brightener and

B1) at least one anionic PA brightener which comprises one or more sulfonic or carboxylic acid groups, and/or B2) at least one nonionic PA brightener.

The nonionic PES brighteners are preferably those of the formulae 1–8, (1)

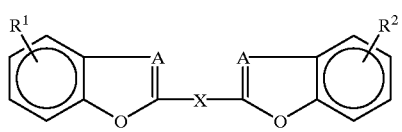

in which $R^1$ and $R^2$ independently of one another are H or $(C_1-C_6)$-alkyl, A=N or C and X is a bond via 1,4-naphthyl, 2,5-thiophene, 2,5-furan, 1,4-phenyl, ethylene, stilbene, styrene or imidazolyl units, (2)

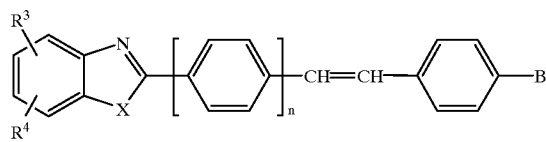

where X=O or S, $R^3$ in position 5 is a hydrogen or chlorine atom or a methyl or phenyl group and $R^4$ is a hydrogen atom, or $R^3$ and $R^4$ are both a methyl group in position 5,6 or 5,7, n is 0 or 1 and B is a cyano or carbo-$(C_1-C_4)$-alkoxy group or a group of the formulae

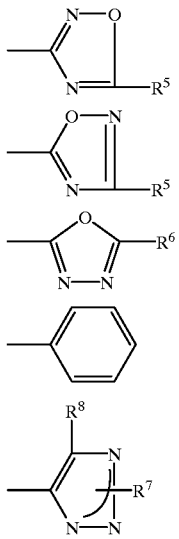

in which $R^5$ is $(C_1-C_6)$-alkyl, $(C_1-C_6)$-chloroalkyl, $(C_1-C_4)$-alkoxy-$(C_1-C_4)$-alkyl, hydroxy-$(C_1-C_4)$-alkyl or a group of the formula $-(CH_2CH_2O)_n-R$, n is 2 or 3 and R is hydrogen or $(C_1-C_4)$-alkyl, $R^6$ is phenyl, halophenyl, $(C_1-C_4)$-alkylphenyl or $(C_1-C_4)$-alkoxyphenyl, $R^7$ is $(C_1-C_4)$-alkyl and $R^8$ is cyano or carbo-$(C_1-C_4)$-alkoxy, (3)

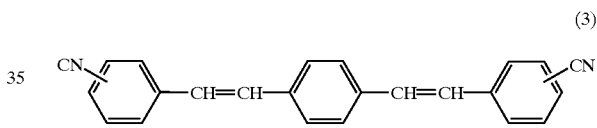

where the CN groups can be located identically or differently in the ortho, meta or para position, (4)

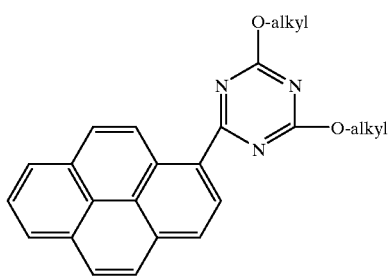

(5)

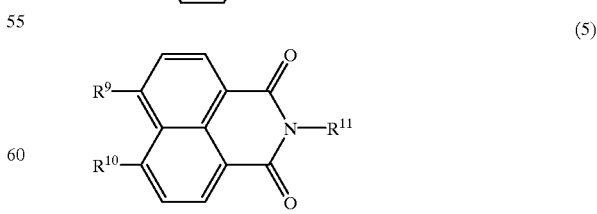

where $R^9$ is hydrogen or alkoxy, $R^{10}$ is alkoxy and $R^{11}$ is alkyl, alkoxyalkyl or dialkylaminoalkyl,

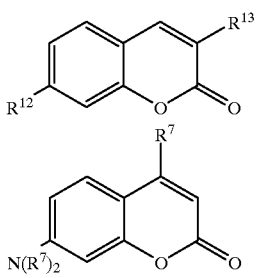
(6)

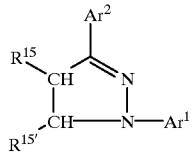
(10)

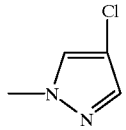
(6a)

where $R^{12}$ is phenyl or the group of the formula and $R^{13}$ is a group of the formula

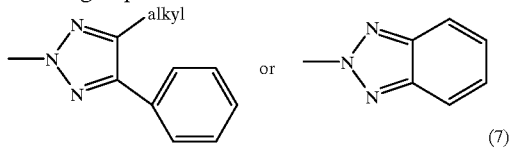

in which $Ar^1$ and $Ar^2$ independently of one another are substituted or unsubstituted aryl radicals and $R^{15}$ and $R^{15'}$, which can be identical or different, are hydrogen, $(C_1-C_4)$-alkyl or phenyl.

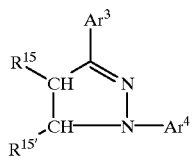
(11)

in which $Ar^3$ and $Ar^4$ independently of one another are phenyl, biphenylyl or naphthyl radicals which may carry further substituents such as hydroxyl, $(C_1-C_6)$-alkyl, $(C_1-C_6)$-alkoxy, halogen, hydroxyalkyl, amino, alkylamino, acylamino, carboxyl, alkoxycarbonyl, sulfonic acid, sulfonic ester, alkylsulfonyl, arylsulfonyl, sulfonyl and sulfonamido groups.

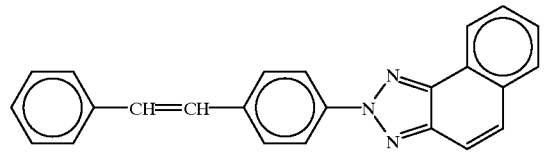
(7)

The anionic PA brighteners include, for example, compounds of the formulae 9 to 14, which are known in the prior art as optical brighteners for cotton, polyamide fibers or protein fibers:

(9)

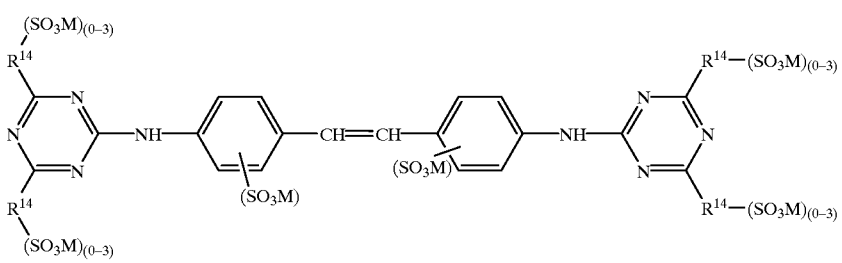

in which $R^{14}$ independently at each occurrence is OH, $NH_2$, O—$(C_1-C_4)$-alkyl, O-aryl, NH—$(C_1-C_4)$-alkyl, N—$((C_1-C_4)$-alkyl$)_2$, N—$((C_1-C_4)$-alkyl)-$((C_1-C_4)$-hydroxyalkyl), N—$((C_1-C_4)$-hydroxyalkyl$)_2$, NH-aryl, morpholino, S—$(C_1-C_4)$-alkylaryl or Cl. M here, as in all other formulae, is $Na^+$, $K^+$, $NH_4^+$ or $NH_{(4-a)}R_a$ where a=1, 2 or 3 and R=$C_1-C_4$-hydroxyalkyl, especially $C_2$-hydroxyalkyl. The stoichiometric indices of the sulfonate groups are dependent on the nature of the radical $R^{14}$, i.e. on how many of such groups this radical is able to carry.

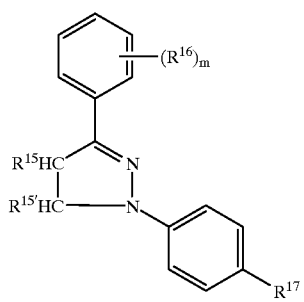
(12)

in which $R^{16}$ is halogen or $(C_1-C_6)$-alkyl, $R^{17}$ is a substituted or unsubstituted $(C_1-C_6)$-alkoxycarbonyl, $(C_1-C_6)$-alkylsulfonyl, sulfonamido or sulfonic acid group, and m is zero, 1, 2 or 3. Further preferred pyrazoline brighteners are represented by the formulae (12a) to (12c):
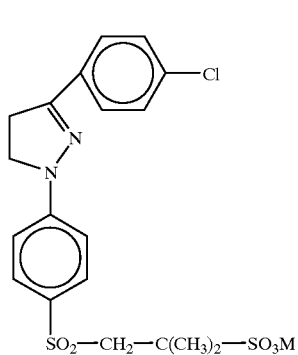
(12a)
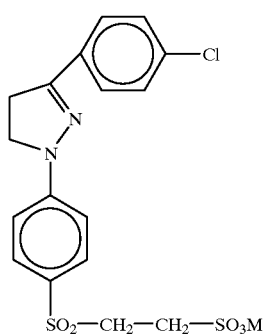
(12b)
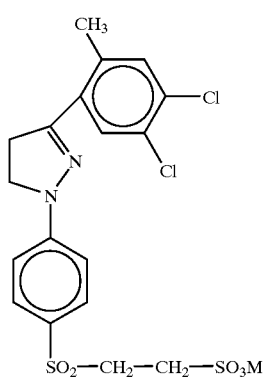
(12c)
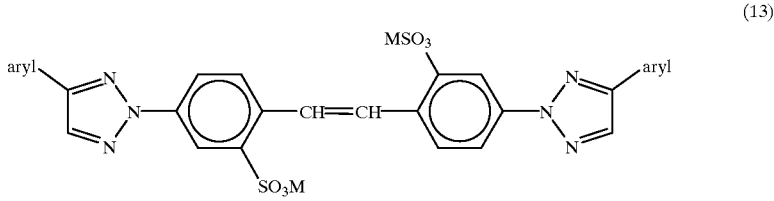
(13)
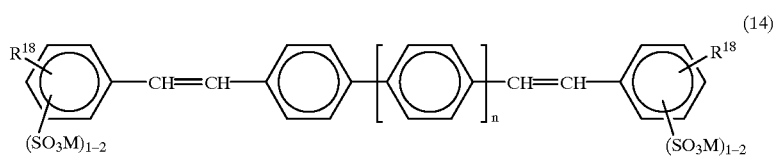
(14)

where $R^{18}$=H, alkyl, oxalkyl, halogen, CN, COO—($C_1$–$C_4$)-alkyl or CO—N[($C_1$–$C_4$)-alkyl]$_2$, and n=0, 1.
Preferred optical brighteners of anionic nature, moreover, are represented by the formulae 15 to 23:
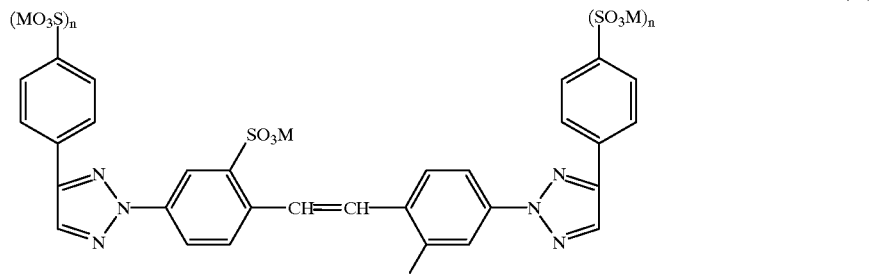
(15)
in which n is 0 or 1,
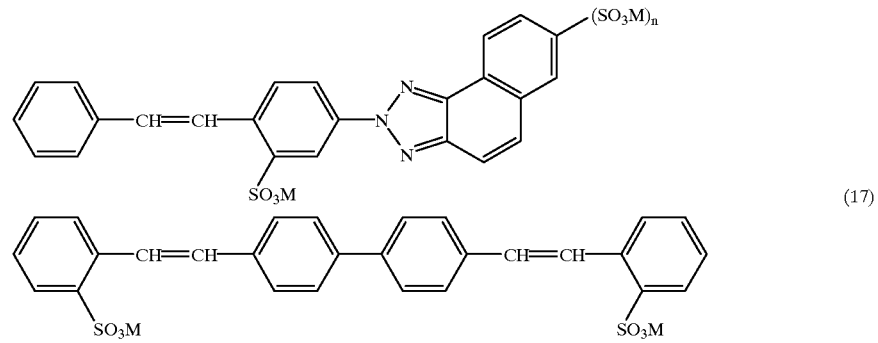
(16)
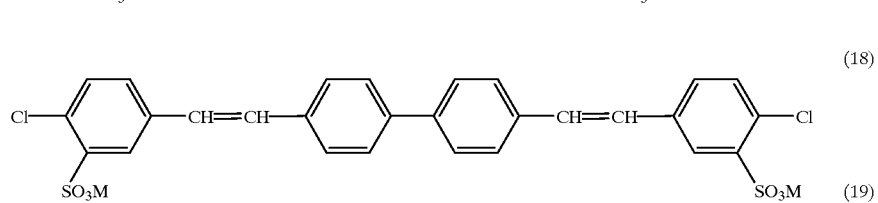
(17)
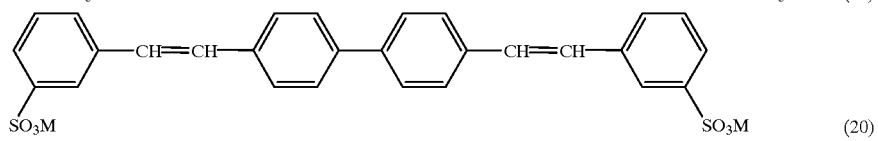
(18)
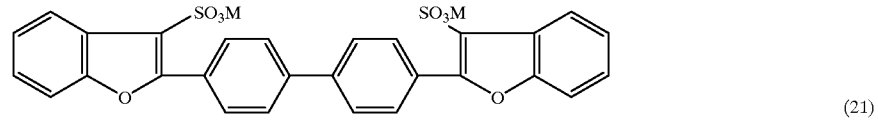
(19)
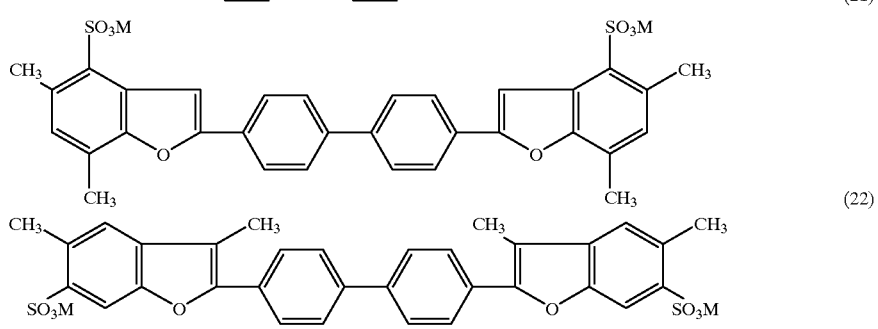
(20)
(21)
(22)
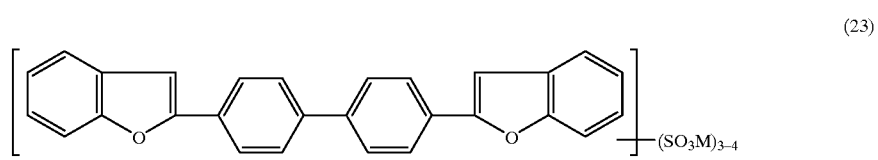
(23)

The formulae 23a and 23are preferred PA brighteners of nonionic nature.

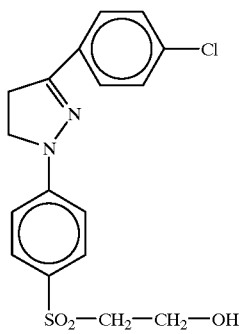

(23a)

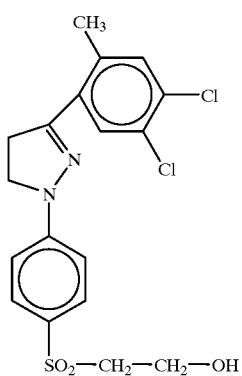

(23b)

Unless specified otherwise "alkyl" is preferably linear or branched $C_1$–$C_{12}$-alkyl, especially $C_1$–$C_6$-alkyl and specifically $C_1$–$C_4$-alkyl. "Aryl" is preferably $C_6$–$C_{18}$-aryl, which may be substituted, and especially phenyl, naphthyl or anthracenyl.

The invention additionally provides a method of brightening fabrics comprising polyamide or polyurethane, which comprises using as brightener a mixture of PES and PA brighteners as described above. In addition to polyamide or polyurethane the fabric may comprise cotton, polyacetate, polyester or other natural or synthetic fibers.

The synergistic effects can be observed in the whitening of nylon 6, nylon 66 and other nylon types, as described, for example, in Winnacker/Küchler, Chem. Technologie (6), pp. 690–698. Using the brightener mixtures of the invention it is also possible with advantage to brighten PA blends comprising synthetic fibers and natural fibers, especially polyamide-polyurethane and polyamide-PES blends.

The mixing ratio for the brighteners of group A (formulae 1–8, polyester brighteners) with brighteners of group B (formulae 9–23, polyamide brighteners) is preferably between 0.05 and 0.95 parts by weight for component A and, accordingly, from 0.95 to 0.05 parts for components B. Components A and component B can in turn contain mixtures of different brighteners from each group in any proportion. Particular preference is given to a mixing ratio of from 5 to 50% by weight for the brighteners of group A and from 95 to 50% by weight of one or more brighteners of group B. The optimum mixing ratio of all the compounds will depend in each individual case on the structure of the respective compound, and can be determined by simple preliminary experiments.

As is customary with optical brighteners, the individual components are brought into the commercial form by dispersing or dissolving them in a liquid medium such as water. In this operation, each of the individual components can be dispersed or dissolved alone and then the dispersions or solutions can be combined. Alternatively, the individual components can be mixed with one another in bulk and then dispersed or dissolved conjointly. The dispersing operation take place in a customary manner in ball mills, colloid mills, bead mills or dispersion kneading equipment. These mixtures are applied under the conditions customary for the use of optical brighteners; for example, by the exhaust process at from 90 to 130° C. with or without reducing agents such as hydrosulfite, hydrogen sulfite or dithionite, for example. Such mixtures are also suitable in neutral, acidic or alkaline hydrogen peroxide bleaching or chlorite bleaching, or by the thermosol process. The water-insoluble brighteners and the mixtures of the invention can also be dissolved in organic solvents such as perchloroethylene or fluorinated hydrocarbons and employed in this solution form. In this case, the textile material can be treated by the exhaust process with the solvent liquor comprising the optical brighteners in solution, or the textile material is impregnated, padded or sprayed with the brightener-containing solvent liquor and then dried at temperatures of 120–220° C., the optical brightener being fixed in the fiber. In this case an outstandingly brightened product is obtained which has excellent light stability and is also resistant to oxidizing and reducing agents. In accordance with the prior art, it is also possible to use selected fading dyes in order to increase the brightener effects still further.

The mixtures of the invention are notable for the fact that they produce outstanding white effects on PA and blends with other fibers. Although it is known that PA can also be brightened with PES brighteners, this application has found little practical use since the PES brighteners either deliver inadequate white effects or else do so but only with an unusable green shade on PA. The mixture of brightener types achieves not only synergistic white effects but also outstanding fastness properties, such as light fastness and weather fastness properties, which are clearly superior to those of the brighteners of group B alone and which surprisingly are raised to the level of the brightener of group A; the absolute values can be very strongly related to the particular article and particular fiber. This is especially important in the case of textiles exposed to intense sunlight, such as swimwear, for example.

EXAMPLES

Fabric sections of PA 6 fibers were washed, dried and impregnated on a pad mangle with the brightener mixture of the invention which comprises either the pure optical brighteners of the formulae 1–8 or mixtures thereof or brighteners of the formulae 9–23 or mixtures thereof or mixtures of the brighteners of the formulae 1–8 with brighteners of the formulae 9–23.

The individual brighteners shown in the examples are commercial products in dispersed or dissolved form, the examples giving the active substance on which the commercial products are based.

The material is squeezed off with a pad mangle between rolls so as to give a defined uptake of moisture. From this the amount of optical brightener applied to the material was calculated. The padded material is subsequently thermosoled on a stenter frame at 190° C. for 30 seconds. The whitenesses indicated in each case are determined by the Ganz formula using a Datacolor instrument. The light fastnesses indicated are determined in accordance with DIN 54 004. Unless noted otherwise, parts are by weight.

The examples using the exhaust process are carried out under the following conditions:

| | |
|---|---|
| x% | optical brightener or brightener mixture, based on the weight of the goods, as indicated for each example |
| 0.5 g/l | of a nonionic wetting agent, e.g. ® Hostapal FA |
| 1 g/l | of a nonionic dispersant, e.g. ® Emulsogen IT |
| 2 g/l | of a reducing agent, e.g; ® Blankit IN |
| pH 4 | established with acetic acid after 30 minutes |

Liquor ratio 40:1
Treat at 95° C. for 45 minutes, then cool and rinse

Examples using the exhaust process

Example 1
Material used: nylon/Lycra 65:35
Brightener used: 0.58% commercial brightener of the formula (12a)
The active content of the product is about 12%. Process as described above.

Example 2

Example 1 is repeated but using 0.7% of a nonionic brightener mixture in dispersed form, consisting of 50 parts of the brightener of the formula (24)

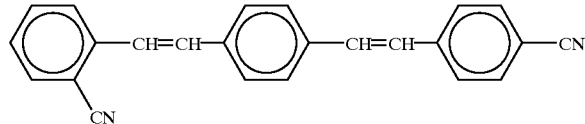

(24)

with 50 parts of the brightener of the formula (25)

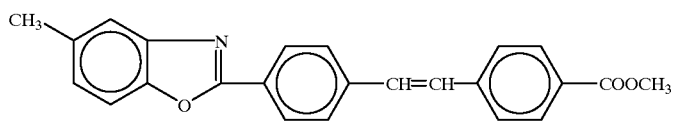

(25)

The active content of the mixture is 10%.

Example 3

Example 1 is repeated but using a mixture consisting of 45.3 parts of the brightener of Example 1 and 54.7 parts of a brightener of Example 2 with a total amount used of 0.64%.
Results of Examples 1–3
(both here and below, V denotes a comparative example and E an example in accordance with the invention)

| Example | 1 (V) | 2 (V) | 3 (E) |
|---|---|---|---|
| Whiteness (Ganz) | 226 | 203 | 226 |
| Shade (Gariz) | −0.8 | 6.2+ | 2.6 |
| LF* | 2–3 | 4 | 4 |

*acc. to DIN 54 004
+ the shade of Ex. 2 is distinctly greenish

Examples 4–6

Examples 1–3 are repeated but without a reducing agent and using a nylon 66 woven as the material to be brightened. Compound (12c) is used as the group B brightener.
Results of Examples 4–6

| Example | 4 (V) | 5 (V) | 6 (E) |
|---|---|---|---|
| Whiteness (Ganz) | 206 | 200 | 207 |
| Shade | −1.36 | 2.7 | 1.7 |
| LF* | 3 | 4 | 4 |

Comparing the light fastness of Example 6 with the prior art values obtained in accordance with Example 4, it is observed that for Example 6 the light fastness is improved by one point.

Examples 7 to 9
Example 7

Prewashed PA 6/6 fabric is padded on a roll mill with 10 g/l of a brightener of the formula (25) and an active content of 10% with a liquor pickup of 60% and a pH of 4.0 (acetic acid) and is then dried and thermosoled at 190° C. for 35 seconds.

Example 8
Example 7 is repeated but with 7.7 g of a 13% formulation of the brightener of the formula (12c).

Example 9
Example 7 is repeated but with a mixture consisting of 5 parts of the brightener formulation of formula (25) and 3.85 parts of the brightener formulation of Example 8.

The whitenesses achieved by the mixture of Example 9 are significantly better than the white effects of Example 7 and 8 for a similar shade. The light fastness values of Example 9 correspond to those of Example 8 and are better by about ½ to 1 point than those for the brightening of Example 7. At the same time, the weather fastness values were raised by about ½–1 point in comparison to Example 8.

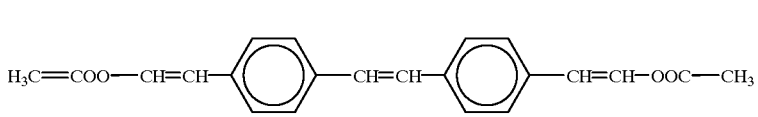

(27)

|  | 7 (V) | 8 (V) | 9 (E) |
|---|---|---|---|
| Whiteness (Ganz) | 152 | 154 | 164 |
| Shade | −0.2 | −0.3 | −0.8 |

Example 10

Example 7 is repeated using a brightener mixture consisting of 80 parts of the brightener of formula (25) and 20 parts of a brightener of the formula (26)

Examples 14–15

Example 13 is repeated but using 10% brightener formulations of the formulae (12a) (Example 14) and (27) (Example 19).

Results of Examples 13–15

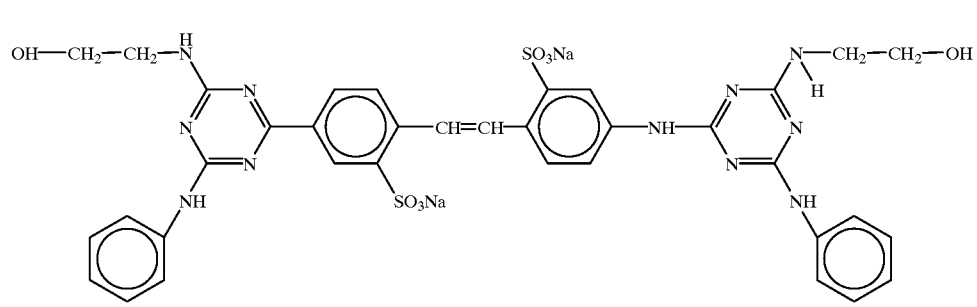

(26)

The overall active content of the brightener mixture is 10%.

Examples 11 and 12

Example 7 is repeated but using in each case 10% formulations of the brighteners (25) and (26) respectively.

Result of Examples 10–12

|  | 13 (E) | 14 (V) | 15 (V) |
|---|---|---|---|
| Whiteness (Ganz) | 146 | 135 | 146 |

|  | 10 (E) | 11 (V) | 12 (V) |
|---|---|---|---|
| Ganz whiteness | 151 | 146 | 83 |

With a bluer shade, Example 13 brings the same white effects as Example 15.

Accordingly, Example 10 exhibits a pronounced synergism.

Example 13

Example 7 is repeated but using a mixture consisting of 40 parts of the brightener of formula (12a) and 60 parts of the brightener of the formula (27). The overall active content of the brightener mixture is 10%.

Example 19

Example 7 is repeated but using 8 g/l of a dispersed brightener mixture consisting of 4.9 parts of the brightener of the formula (3) and 2.1 parts of the brightener of the formula (25) and 2 g/l of the brightener of the formula (28) with an active content of 15%.

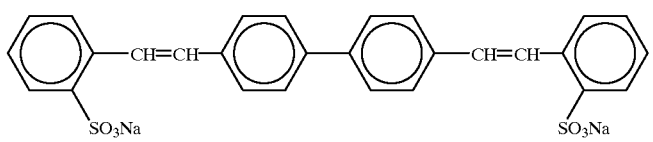

(28)

Examples 20 and 21

Example 19 is repeated but using 10 g/l of a dispersed form of the brightener mixture consisting of 5.25 parts of the brightener of the formula (29)

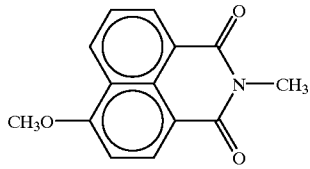

(30)

and 40parts of the brightener of the formula (31) (10% active substance)

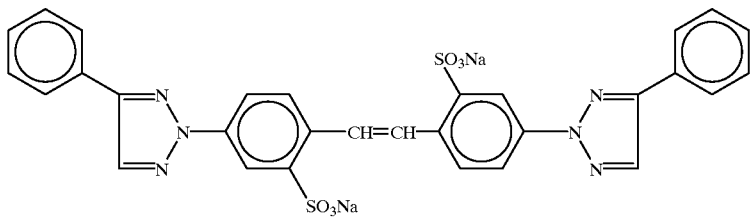

(31)

Examples 23 and 24

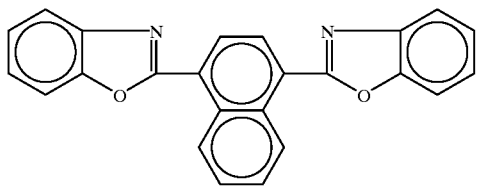

(29)

Example 7 is repeated but using 10 percent brightener formulations of the formulae (30) and (31).

Results of examples 22 to 24

| Ex. | 22 (E) | 23 (V) | 24 (V) |
| --- | --- | --- | --- |
| Whiteness (Ganz) | 116 | 104 | 114 | and 1.75 parts of the brightener of the formula (25).

In the case of Example 21, a commercial solution of a 15% brightener formulation of the formula (28) is used.

Results of Examples 19 to 21

| Ex. | 19 (E) | 20 (V) | 21 (V) |
| --- | --- | --- | --- |
| Whiteness (Ganz) | 170 | 168 | 137 |

Example 22

Example 7 is repeated but using a mixture consisting of 60 parts of the brightener (30) (10% active substance)

We claim:

1. A mixture of optical brighteners comprising

A) at least one nonionic polyester brightener and

B1) at least one anionic polyamide brightener which comprises one or more sulfonic or carboxylic acid groups;

having a mixing ratio of polyester brightener (component A) to polyamide brightener (component B1) wherein a synergistic effect is achieved.

2. A mixture as claimed claim 1, wherein the nonionic polyester brightener is at least one compound of the formulae

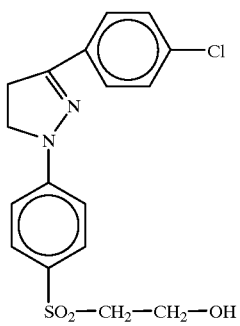
(23a)

or

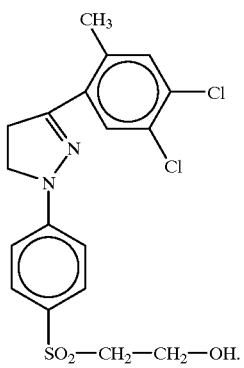
(23b)

3. A mixture as claimed in claim 1, wherein a mixing ratio of polyester brightener (component A) to polyamide brightener (component B1 lies between 95% by weight polyester brightener to 5% by weight polyamide brightener and 5% by weight polyester brightener to 95% by weight polyamide brightener.

4. A method of brightening a fabric comprising polyamide or polyurethane, which comprises the steps of:
   providing a fabric comprising polyamide or polyurethane;
   providing a mixture as claimed in claim 3; and
   applying said mixture to said fabic.

5. A method of brightening a fabric comprising polyamide or polyurethane, which comprises the steps of:
   providing a fabric comprising polyamide or polyurethane or polyamide-polyurethane blend, said fabric optionally further contains fibers selected from cotton, polyacetate or polyester;
   providing a mixture as claimed in claim 3; and
   applying said mixture to said fabic.

6. A mixture of optical brighteners as claimed in claim 1, wherein the nonionic polyester brightener (component A) is at least one compound of the formulae 1–8:

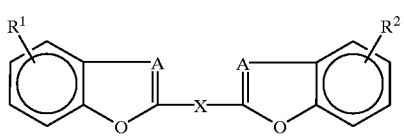
(1)

in which $R^1$ and $R^2$ independently of one another are H or $(C_1-C_6)$-alkyl, A=N or C and X is a bond via 1,4-naphthyl, 2,5-thiophene, 2,5-furan, 1,4-phenyl, ethylene, stilbene, styrene or imidazolyl units,

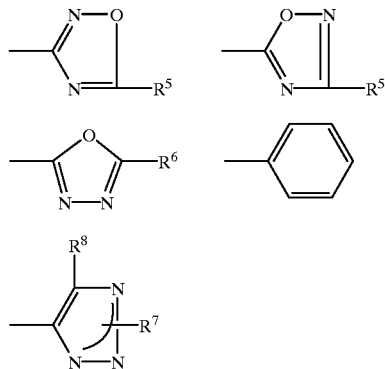
(2)

where X is O or S, $R^3$ in position 5 is a hydrogen or chlorine atom or a methyl or phenyl group and $R^4$ is a hydrogen atom, or $R^3$ and $R^4$ are both a methyl group in position 5,6 or 5,7, n is 0 or 1 and B is a cyano or carbo-$(C_1-C_4)$-alkoxy group or a group of the formulae in which $R^5$ is $(C_1-C_6)$-alkyl, $(C_1-C_6)$-chloroalkyl, $(C_1-C_4)$-alkoxy-$(C_1-C_4)$-alkyl, hydroxy-$(C_1-C_4)$-alkyl or a group of the formula -$(CH_2CH_2O)_n$—R, n is 2 or 3 and R is hydrogen or $(C_1-C_4)$-alkyl, $R^6$ is phenyl, halophenyl, $(C_1-C_4)$-alkylphenyl or $(C_1-C_4)$-alkoxyphenyl, $R^7$ is $(C_1-C_4)$-alkyl and $R^8$ is cyano or carbo-$(C_1-C_4)$-alkoxy,

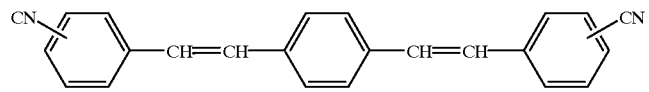
(3)

where the CN groups can be located identically or differently in the ortho, meta or para position,
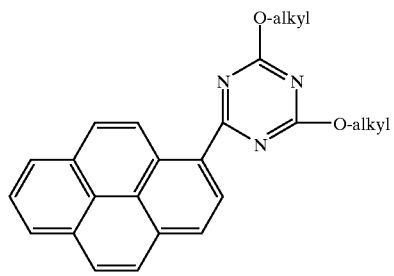
(4)
where $R^9$ is hydrogen or alkoxy, $R^{10}$ is alkoxy and $R^{11}$ is alkyl, alkoxyalkyl or dialkylaminoalkyl,
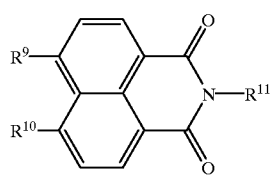
(5)
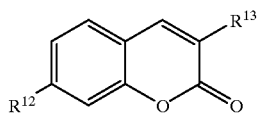
(6)
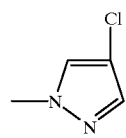
(6a)
where $R^7$ is $(C_1-C_4)$-alkyl, $R^{12}$ is phenyl or the group of the formula
and $R^{13}$ is a group of the formula
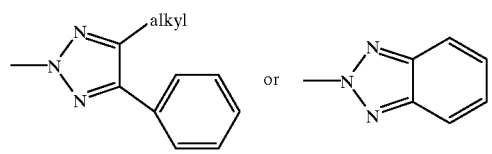
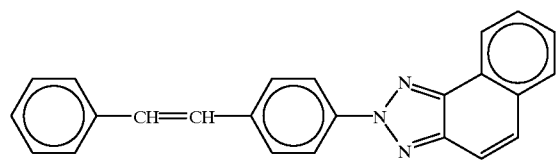
(7)
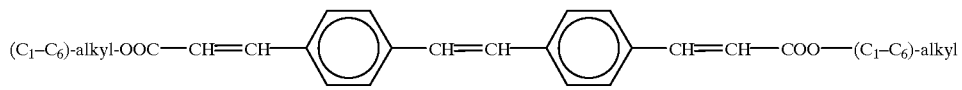
(8)

7. A mixture as claimed in claim 1, wherein the anionic polyamide brightener (component B1) is at least one compound of the following formulae:

(9)

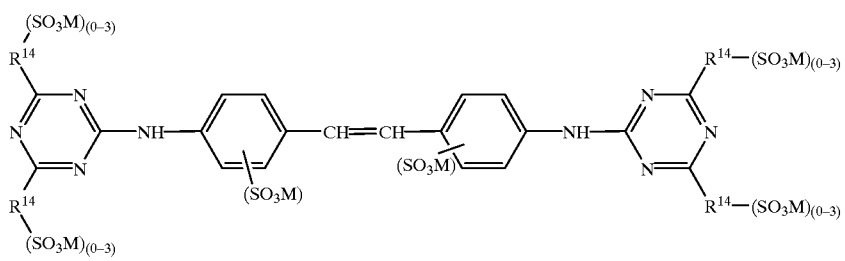

in which $R^{14}$ independently at each occurrence is OH, $NH_2$, O—$(C_1-C_4)$-alkyl, O-aryl, NH—$(C_1-C_4)$-alkyl, N—$((C_1-C_4)$-alkyl$)_2$, N—$((C_1-C_4)$-alkyl$)$-$((C_1-C_4)$-hydroxyalkyl), N—$((C_1-C_4)$-hydroxyalkyl$)_2$, NH-aryl, morpholino, S—$(C_1-C_4)$-alkylaryl or Cl and M is $Na^+$, $K^+$, $NH_4^+$ or $NH_{(4-a)}R_a$ where a=1, 2 or 3 and R=$C_1-C_4$-hydroxyalkyl, stoichiometric indices of sulfonate groups being dependent on the nature of radical $R^{14}$;

(10)

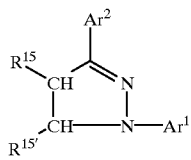

in which $Ar^1$ and $Ar^2$ independently of one another are substituted or unsubstituted aryl radicals and $R^{15}$ and $R^{15'}$, which can be identical or different, are hydrogen, $(C_1-C_4)$-alkyl or phenyl;

(11)

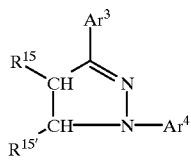

in which $Ar^3$ and $Ar^4$ independently of one another are phenyl, biphenylyl or naphthyl radicals which optionally carry further substituents selected from the group consisting of hydroxyl, $(C_1-C_6)$-alkyl, $(C_1-C_6)$-alkoxy, halogen, hydroxyalkyl, amino, alkylamino, acylamino, carboxyl, alkoxycarbonyl, sulfonic acid, sulfonic ester, alkylsulfonyl, arylsulfonyl, sulfonyl and sulfonamido groups;

(12)

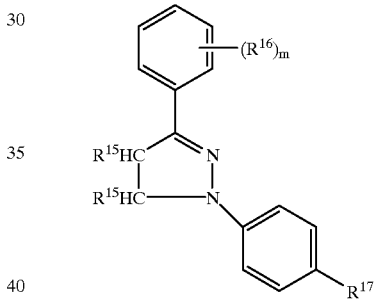

in which $R^{16}$ is halogen or $(C_1-C_6)$-alkyl, $R^{17}$ is a substituted or unsubstituted $(C_1-C_6)$-alkoxycarbonyl, $(C_1-C_6)$-alkylsulfonyl, sulfonamido or sulfonic acid group, and m is zero, 1, 2 or 3;

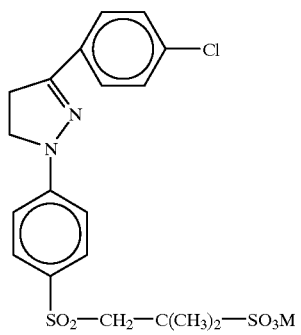
(12a)
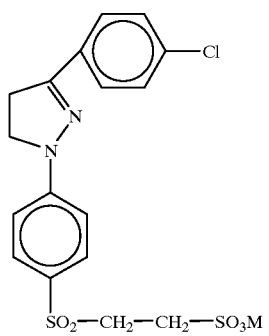
(12b)
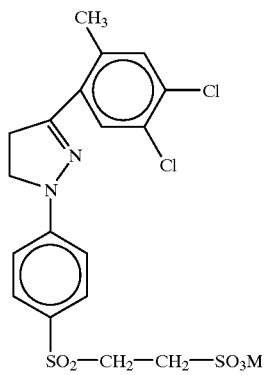
(12c)
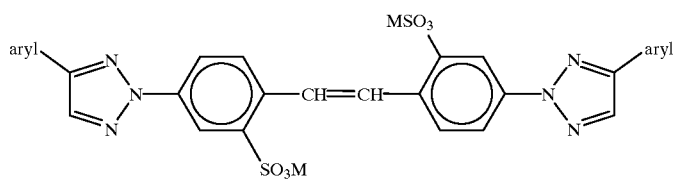
(13)
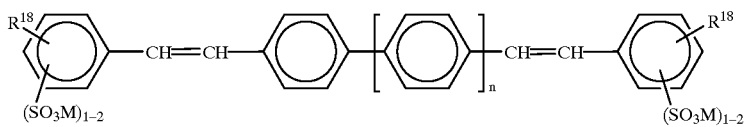
(14)

where $R^{18}$=H, alkyl, oxalkyl, halogen, CN, COO—$(C_1$–$C_4)$-alkyl or CO—N[$(C_1$–$C_4)$-alkyl]$_2$, and n=0, 1;
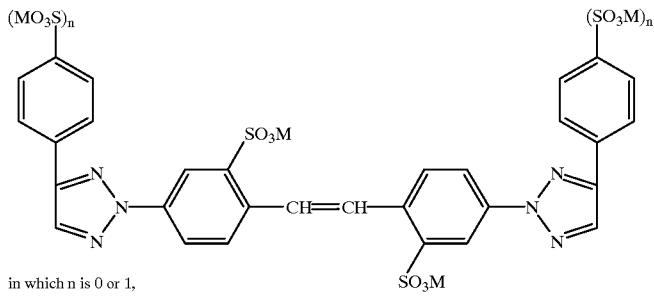 (15)
in which n is 0 or 1,
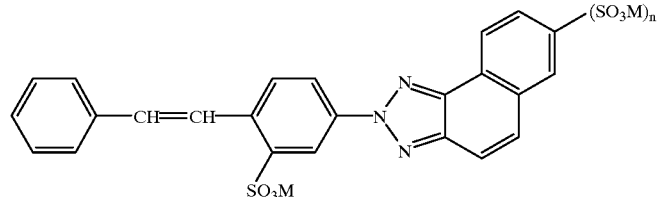 (16)
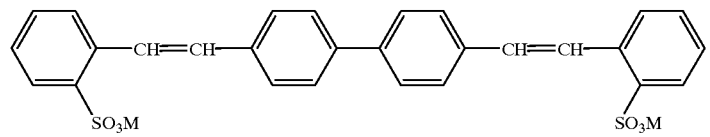 (17)
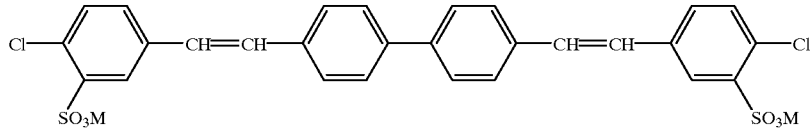 (18)
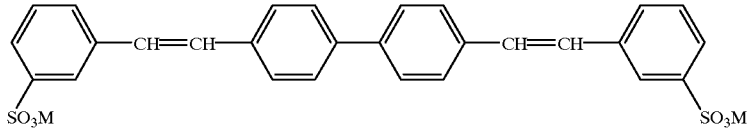 (19)
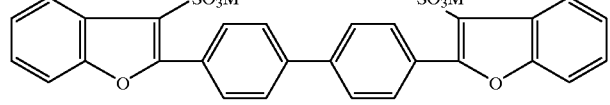 (20)
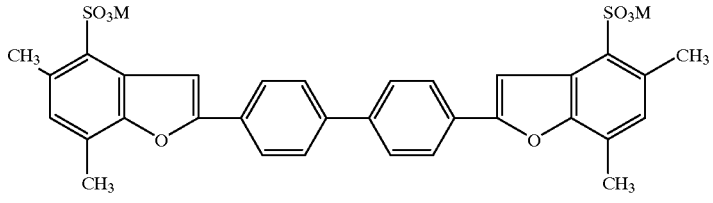 (21)
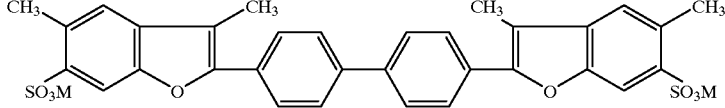 (22)
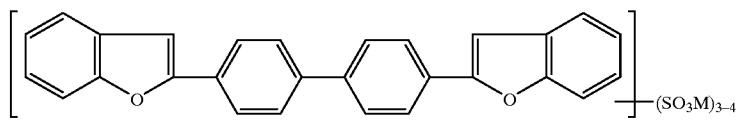 (23)
* * * * *